United States Patent

Muharib

[11] Patent Number: 5,904,665
[45] Date of Patent: *May 18, 1999

[54] AUTOMATED PROLONGED SLOW RELEASE INTRAUTERINE INSEMINATION USING SELF RETAINING INTRAUTERINE INSEMINATION CATHETER

[75] Inventor: Nabil Sefein Muharib, Salmyia, Kuwait

[73] Assignees: Vance Products Inc.; Cook Urological Inc., both of Spencer, Ind.

[*] Notice: This patent is subject to a terminal disclaimer.

[21] Appl. No.: 08/399,479

[22] Filed: Mar. 7, 1995

[51] Int. Cl.$^6$ .................................................. A61M 31/00
[52] U.S. Cl. ............................. 604/55; 604/104; 606/193
[58] Field of Search ................................. 604/55, 96, 28, 604/49, 130, 45, 131, 906, 73, 27, 97, 99, 104; 606/119, 193; 600/33, 35

[56] References Cited

U.S. PATENT DOCUMENTS

| | | | |
|---|---|---|---|
| 4,280,501 | 7/1981 | Foderick | 604/99 X |
| 4,432,753 | 2/1984 | Cassou et al. | 604/55 |
| 4,533,345 | 8/1985 | Louw | 604/43 |
| 4,547,188 | 10/1985 | Bolduc | 604/55 |
| 4,654,025 | 3/1987 | Cassou et al. | 604/55 |
| 4,790,814 | 12/1988 | Fischl et al. | 604/27 |
| 5,372,584 | 12/1994 | Zink et al. | 606/193 X |
| 5,536,243 | 7/1996 | Jeyendron | 600/35 |
| 5,562,654 | 10/1996 | Smith | 604/892.1 |

OTHER PUBLICATIONS

Muharib et al, "Slow Release Intrauterine Insemination Versus the Bolus Technique in the Treatment of Women with Cervical Mucus Hostility," Human Reproduction, vol. 7, No. 2, pp. 227–229, 1992.

Muharib and Gadir; Abstract from the X111 World Congress on Fertility and Sterility, Oct. 1989.

*Primary Examiner*—Michael Buiz
*Assistant Examiner*—A. T. Nguyen
*Attorney, Agent, or Firm*—Richard J. Godlewski

[57] ABSTRACT

A method of automated prolonged slow release artificial intrauterine insemination is disclosed wherein motile sperm are introduced into the uterus in a programmed, organized and metered pattern over an extended period of time. A catheter is inserted into the uterine cavity and aliquots of sperm containing medium are injected at a rate of 10 to 20 mm/hr (approximately every 30 seconds) for between 4 to 6 hours. The motile sperm content of each aliquot is between 8,000 to 75,000. Preferably, the method is carried out with the use of a novel delivery device. The device of the present invention comprises a flexible catheter having a delivery channel, a first end attachable to a pumping means, and a second end (uterine end) adapted to pass through the cervix and into the uterine cavity. The catheter is provided with an inflatable balloon adjacent the second end. Upon inflation of the balloon, the catheter is immobilized in the vagina. The pumping means delivers the aliquots of sperm containing medium through the delivery channel and into the uterus. The pumping means is adapted to pump sufficient medium to deliver between 1 million to 9 million motile spermatozoa per hour into the uterine cavity. The balloon is deflatable to permit the catheter's easy removal after use. Preferably, the pumping means may be strapped to the abdomen of the patient to permit the patient to leave the treatment center during the treatment period.

21 Claims, 2 Drawing Sheets

AUTOMATED PROLONGED SLOW RELEASE INTRAUTERINE INSEMINATION USING SELF RETAINING INTRAUTERINE INSEMINATION CATHETER

FIELD OF THE INVENTION

The present invention relates to artificial intrauterine insemination.

BACKGROUND OF THE INVENTION

Artificial insemination attempts to treat infertile couples by solving their infertile problems. One of the main causes of infertility is that small numbers or none of the ejaculated spermatozoa reach the egg in the ampullary portion of the tube. Oligozoospermia (small sperm number in the ejaculate), asthenozoospermia (decreased sperm motility), low semen volume, and hostile cervical mucus are the common reasons for this occurrence. These factors are clinically diagnosed by persistently negative or poor postcoital tests, i.e., absence of sperms or motile sperms in the secretion of the uterine cervix after natural sexual intercourse.

Intrauterine insemination (IUI) with husband's semen is widely used in the treatment of infertile couples with cervical mucus hostility and moderately deranged male semenograms. The intrauterine insemination consists of a bolus, one-off injection into the uterine cavity of a large number of motile, washed and concentrated sperms condensed in a small volume of 0.2 to 0.4 ml. of culture media. This is the classical (conventional) bolus intrauterine insemination technique. An important disadvantage of the classical IUI bolus technique is the deposition of very large number of sperms into the uterine cavity. This may have an adverse immunological impact, and may cause polyzoospermia. Spermatozoa placed in the uterine cavity migrates quickly to the fallopian tubes and uterine cavity. Hence, the period time of fertilisation is limited and IUI has to be perfectly coordinated with ovulation for fertilization to take place. As a result of these disadvantages, the conception rate for classical IUI is very low.

To perform classical IUI an insemination catheter is used to introduce the semen into the uterine cavity through the cervix. This catheter is removed immediately after the introduction of the sperms into the uterine cavity.

SUMMARY OF THE INVENTION

In the method of the present invention, motile sperm are introduced into the uterus over an extended period of time. A catheter is inserted into the uterus and aliquots of sperm containing medium are injected every 30 seconds for between four to six hours. The motile sperm content of each aliquot is approximately between 8,000 to 75,000.

The device of the present invention comprises a flexible catheter having a delivery channel, a first end attachable to a pumping means, and a second end adapted to pass through the cervix and into the uterus. The catheter is provided with an inflatable balloon adjacent the second end. Upon inflation of the balloon, the catheter is immobilized in the vagina.

The device of the present invention may also comprise a portable pumping means for delivering aliquots of sperm containing medium through the delivery channel and into the uterus. The pumping means is adapted to pump a volume of medium through the catheter over several hours. The pumping means may be strapped to the abdomen of the patient to permit the patient to leave the treatment centre during the treatment period.

BRIEF DESCRIPTION OF THE DRAWINGS

A catheter constructed in accordance with the present invention will now be described, by example only, reference being had to the accompanying drawings, in which.

DETAILED DESCRIPTION OF THE INVENTION

The method of the present invention is a treatment for female infertility comprising the slow delivery of motile sperm containing media to the uterus of the ovulating patient at the rate of between 8,000 to 75,000 sperm per 30 second interval. The media is delivered to the uterus by means of a metering pump and a stabilized flexible catheter inserted into the uterus. The motile sperm are introduced into the uterus over four to six hours. The sperm metering pump can be strapped to the patients abdomen to permit the patient to move about or return home during the treatment period.

The sperm containing medium is prepared by first collecting a quantity of semen into a sterile container. The sperm concentration and motility of the semen sample are determined. A sperm wash in a sterile BWW media with 0.3% human albumen is performed in a standard two-step sequence. The sperms are then overlaid with media and the swim up portion of the specimen collected. The concentration of swim up portion is then adjusted to $15 \times 10^6$ motile sperm per ml. It will be appreciated that other methods of producing motile sperm containing media are known, and can be utilized in the present method. While the desired concentration of $15 \times 10^6$ motile sperm per ml of medium is optimal, it is anticipated that concentrations of between $10 \times 10^6$ motile sperm per ml to $40 \times 10^6$ motile sperm per ml may be used.

Figures 1, 2:
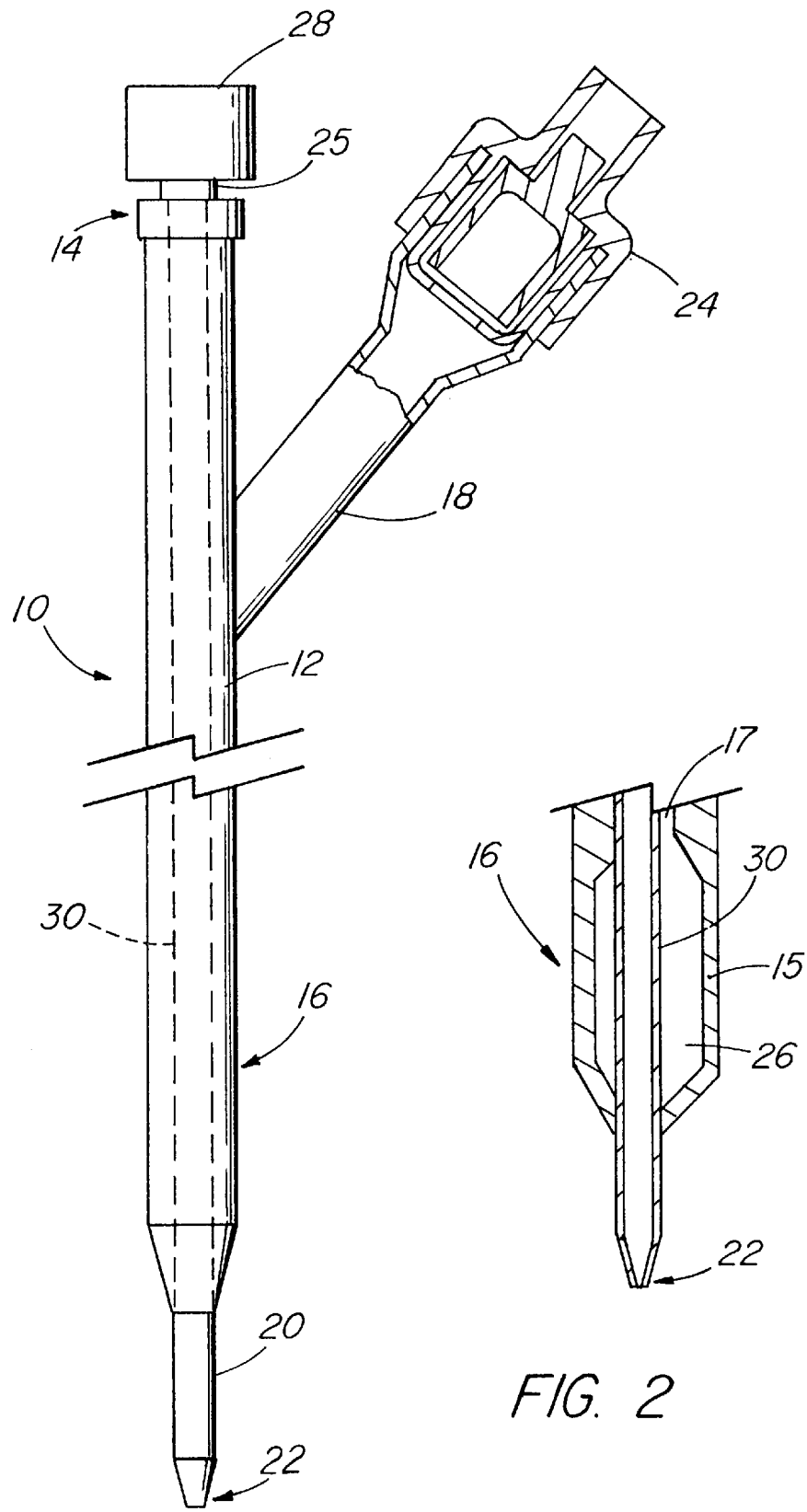
FIG. 1 is a side view of the catheter portion of the invention.
FIG. 2 is a long sectional view of a portion of the catheter shown in FIG. 1.

The catheter portion of the invention will now be described. Referring firstly to FIG. 1, the catheter, shown generally as item 10, comprises a flexible tubular body 12 having a proximal end 14 and a distal end 22. Proximal end 14 is adapted to fit in the patient's vagina and distal end 22 is adapted to be inserted into the uterus. Body 12 is preferably made of a flexible silicone rubber, and has an outside diameter of 6.7 mm (0.263 inches or 20 French). The diameter of the body of the catheter can vary between 4 to 8 mm. The catheter is provided with a narrow distal portion or extension 20 near distal end 22. The diameter of distal portion 20 is 2.7 mm (0.105 inches or 8 French), and is sufficiently narrow to pass through the cervix without difficulty. The diameter of distal portion 20 can vary between 1.5 to 4 mm. For ease of insertion and comfort, distal portion 20 is also formed from a flexible silicone rubber material. Distal portion 20 is a hollow tube with an internal diameter of 0.044 inches. The overall length of catheter 10 is 25 cm and the length of distal portion 20 is preferably 5 cm. The length of distal portion 20 can vary between 4 cm to 7 cm. It will be understood that the lengths and widths of catheter 10 and distal portion 20 can be varied to suit the needs of the patient.

Figure 3:
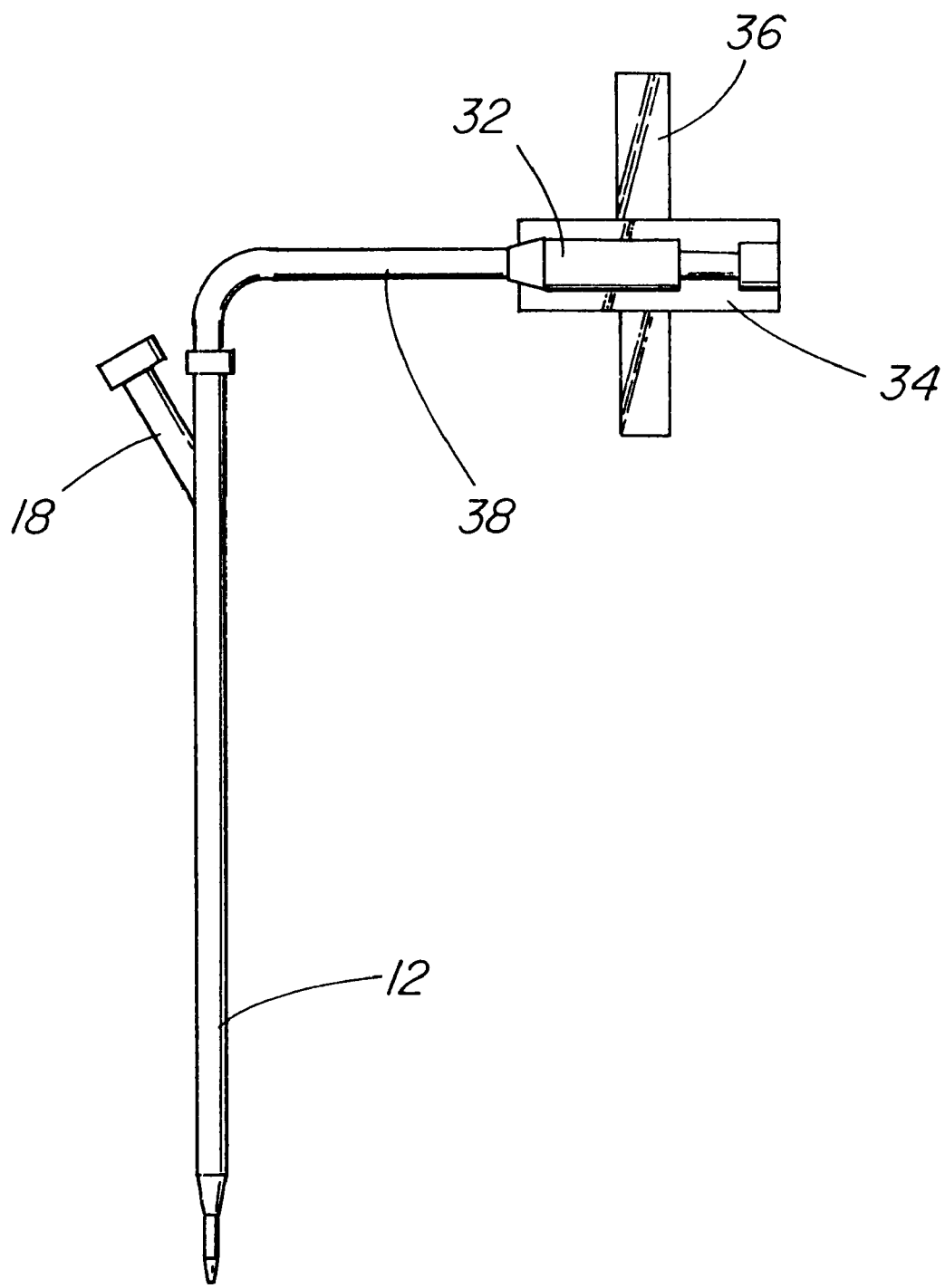
FIG. 3 is a side view of the catheter portion of the invention attached to the sperm delivery pump.

As seen in FIGS. 1, 2 and 3, distal portion 20 is an extension of hollow tube 30 that extends the length of body 12. Proximal portion 25 of tube 30 passes through end 14 of body 12. Proximal portion 25 can be connected to the end of a syringe 32 either directly or via flexible silicone rubber connecting tube 38. Removable cap 28 covers the end of proximal portion 25 until the catheter is ready to use.

Catheter 10 is provided with stabilizing or releasable retention means such as a balloon 16 adjacent distal portion 20 for stabilizing or releasably retaining the catheter in the uterus. Balloon 16 comprises a modified portion of body 12 having elastic walls 15. Elastic walls 15 are separated from tube 30 by space 26, which is in turn connected to hollow inflation tube 18 via passage 17. The inflation tube is embedded in the body of the catheter, the proximal end of the inflation tube exiting the body of the catheter at a point adjacent proximal end 14 of the catheter. Passage 17 connects balloon 16 to female connector element 24. Balloon 16 can be inflated by injecting saline, or some other suitable fluid, through female connector element 24. Pumping fluid into balloon 16 causes space 26 to expand and thereby expanding the diameter of the catheter. By inflating balloon 16 after distal portion 20 of the catheter has been inserted into the cervix, the catheter is immobilized in the vagina.

The catheter has a number of advantages. Firstly, the moderate rigidity of the catheter permits distal portion 20 to be inserted into the uterine cavity through the cervical canal with the aid of only a vaginal speculum for exposing the cervix. A simple ovum forceps may be used to hold the balloon in its place in the vagina, after inflation, while the speculum is removed. The balloon immobilises the catheter in the vagina and in the uterus. The catheter can be easily removed by first deflating the balloon and then gently pulling the catheter out. The balloon can be deflated by aspiring back the saline from the balloon with any syringe. Alternatively, the catheter could be cut with a pair of ordinary scissors and the saline emptied.

The catheter of the present invention can be used with bolus IUI, intracervical insemination or even vaginal insemination. When used with one of these insemination techniques, the balloon portion of the catheter also serves as a valve against leakage of sperms from the vagina in cases of draw back of washed sperms from the uterine cavity.

To practice the method of the invention on an ovulating patient, the motile sperm containing medium is loaded into syringe 32, and the syringe is placed in a portable pulsatile syringe driver 34. While the patient is in a supine position, the cervix is exposed with a bivalve speculum and the distal portion 20 of the catheter is inserted into the cervix. Cap 28 is removed and proximal portion 25 of the catheter is attached to the syringe. Female connector element 24 is attached to a saline pump (not shown) and the balloon is inflated sufficiently to immobilize the catheter in the vagina. The speculum is then removed. The syringe 32 and driver 34 are then strapped to the patient's abdomen with the aid of straps 36.

After the catheter is properly inserted, pulsatile syringe driver 34 is turned on. The Syringe 32 and syringe driver 34 are calibrated to release a single aliquot every 30 seconds, each aliquot containing approximately between 8,000 to 75,000 motile sperm. Assuming the motile sperm concentration of the medium to be $15 \times 10^6$ per ml, each aliquot will be between $0.53 \times 10^{-3}$ ml to $5.1 \times 10^{-3}$ ml in volume. The catheter is left in place or between four to six hours. However, it is to be understood that the syringe driver can be adapted to pump aliquots of media having volumes of between $1 \times 10^{-3}$ ml to $10 \times 10^{-3}$ ml each at intervals between ten seconds to one minute.

The patient may be allowed to return home to rest during the treatment. Since the catheter is immobilized by the inflation of balloon 16, distal portion 20 does not dislodge and syringe driver 34 continues to deliver motile sperm to the patient's uterus at the rate of between 1 million to 9 million sperm per hour for the entire treatment interval. After the elapsed treatment interval, the patient deflates balloon 16 of the catheter by either opening a valve at the female connector element 24 or by cutting the catheter. When balloon 16 is deflated, the catheter can be removed by gently pulling on body 12.

Syringe 32 and driver 34 form a pumping mechanism. While the method has been described using a pulsating syringe driver, it can be appreciated that a continuous syringe driver can also be used, provided that motile sperm are being delivered to the uterus at the rate of between 1 million to 9 million sperm per hour. Other types of pumping mechanisms adapted to slowly release minute volumes over several hours may be used.

The treatment period should be between four to six hours. It is anticipated that slightly longer or shorter time periods could also be used. Preferably the motile sperm concentration for the medium is $15 \times 10^6$ sperms per ml, but it is anticipated that sperm concentrations of between $10 \times 10^6$ to $40 \times 10^6$ motile sperm per ml would be useful.

The volume of each aliquot will have to be adjusted to maintain the desired motile sperm delivery rate and to keep the volume of each aliquot to just a few microliters. It has been discovered that if the volume of medium delivered into the uterus is no greater than a few micro liters, there is a decreased chance of cramping and discomfort.

As mentioned above, the motile sperm delivery rate is between 1 to 9 million sperm per hour. Preferably, the sperm delivery rate is 3 million sperm per hour. If the sperm concentration of the sperm medium is $15 \times 10^6$ sperms per ml, then the preferred delivery rate will be approximately $1.7 \times 10^{-3}$ ml (25,000 sperms) per 30 second interval.

It has been discovered that the slow release into the uterus of relatively low concentrations of motile sperm over several hours increases the chances of conception. By slowly and continuously introducing sperm at a rate of between 1 to 9 million sperm per hour, a reservoir of motile sperm is accumulated in the uterine cavity and cervical canal, thereby prolonging the period of potential fertilization.

EXPERIMENTAL TRIAL

The method of the present invention will now be further explained by presenting the following experimental results. Thirty nine infertile women with cervical mucus hostility were divided at random into two groups for slow release IUI (SR-IUI) with prepared husbands semen. Diagnosis was made by repeated negative post coital tests (PCT) performed 8 to 12 hours after sexual intercourse with good cervical mucus biophysical characteristics and positive crossed hostility tests using Penetrak bovine mucus. All patients had normal ovulatory cycles with normal hysterosaplingograms and pelvic laparoscopic findings. The husbands' semen analyses were repeatedly normal. Sperm density exceeded $20 \times 10^6$ per ml with 40% minimum active motility and 70% normal forms. Semen cultures for aerobic and anaerobic micro organisms were negative. Serum antispermatozoal antibodies were not detected in all patients using tray agglutination and immobilization tests.

The sperm containing media was prepared as follows. Split ejaculate of semen was collected into a sterile container and sperm concentration and motility were determined. Sperm wash in a sterile BWW medial with 0.3% human albumen was performed in a standard two-step sequence.

Sperms were then overlaid with media and the swim up portion of the specimen collected. The sperm concentration was readjusted to $15 \times 10^6$ motile sperm per ml. The sperm containing media was placed in a syringe loaded on a pulsatile syringe driver.

Twenty women started with SR-IUI of $3 \times 10^6$ motile sperm per hour (treatment A), nineteen with SR-IUI of $9 \times 10^6$ motile sperm per hour (treatment B) in a cross-over study for four alternating cycles. Insemination was timed 36–40 hours after injection of 5000 IU of human chorionic gonadotrophin at a follicular diameter of 18 mm during ultrasonically monitored cycles or positive LH surge in urine.

With the patient in the supine position, the cervix was exposed with a bivalve speculum. A self stabilizing feeding catheter (item 10 as illustrated in FIG. 1) was fixed to the syringe and introduced into the uterine cavity. The catheter was inflated and the speculum was then released and removed. The auto-syringe drivers were adjusted to deliver 3 million motile sperm per hour in treatment A and 9 million motile sperm per hour in treatment B. Pulses were timed at 30 second intervals The auto-syringe was strapped to the patients abdomen to permit the patients to leave the clinic. The treatment period was four hours in each case.

Eighteen pregnancies were achieved, 15 from 62 cycles of treatment A and 3 from 54 cycles of treatment B (Chi-Square, P<0.05). The cumulative pregnancy rate was 64.7% and 18.7% after treatments A and B respectively. This small randomized cross-over study showed that the pregnancy rate was significantly higher after continuous SR-IUI of small sperm number ($3 \times 10^6$ sperm/hr). The higher pregnancy rate observed after treatment A in this study may indicate that small number of motile sperm ($3 \times 10^6$ sperm/hour) are required for slow release IUI, but in a continuous pattern. It is anticipated from these results that sperm delivery rates as low as 1 million per hour should also be effective.

As can be seen from the experimental results, the slow release of motile semen over a prolonged period of time is effective in treating infertility. It is believed that the added comfort and ease provided by a portable slow release artificial insemination device may result in higher rates of conception. Furthermore, the patient suffers less discomfort and is able to leave the medical facility earlier as a result of the portability of the artificial insemination device.

While the method of automated prolonged slow release intrauterine insemination using the self retaining intrauterine insemination catheter has been illustrated and described with respect to the preferred embodiment, it will be appreciated by those skilled in the art that numerous variations of these embodiments may be made without departing from the scope of the invention.

Therefore what is claimed is:

1. A method of artificial intrauterine insemination comprising:
    delivering a motile sperm containing media to a patient's uterus by means of a flexible catheter and a pump, the catheter having a first end dimensioned to be insertable through the cervix and into the uterus and stabilizing means attached adjacent the first end for stabilizing the catheter in the uterus, the catheter having a second end adapted to be attachable to the pump;
    positioning the first end of the catheter in the uterus;
    positioning the stabilizing means in the vagina of the patient;
    selecting the concentration of the sperm containing media and the pumping rate of the pump to deliver between 1 million and 9 million motile sperm per hour; and
    the pump pumping the media into the uterus for at least three hours and the pump pumping the media in a series of aliquots.

2. A method of artificial intrauterine insemination as described in claim 1 wherein the pump is portable and is provided with an attachment means for releasably attaching the pump to the patient's body.

3. A method of artificial intrauterine insemination as described in claim 1 wherein the pump comprises a pulsing syringe pump.

4. A method of artificial intrauterine insemination as described in claim 1 wherein the pulsing syringe pump pumps each aliquot in intervals of less than one minute.

5. A method of artificial intrauterine insemination as described in claim 4 wherein the volume of each aliquot is less than $3 \times 10^{-3}$ ml.

6. A method of artificial intrauterine insemination as described in claim 5 wherein the concentration of the motile sperm containing media and the pumping rate of the pulsing syringe pump are adjusted to deliver 3 million motile sperm per hour.

7. A method of artificial intrauterine insemination as described in claim 6 wherein the concentration of the motile sperm containing media is between $10 \times 10^6$ to $40 \times 10^6$ motile sperm per ml, and wherein the pulsing syringe pump pumps an aliquot of sperm containing media approximately every thirty seconds, and wherein the pulsing syringe pump pumps the media for between four to six hours.

8. A method of artificial intrauterine insemination comprising:
    delivering a motile sperm containing media to a patient's uterus by means of a flexible catheter and a pump, the catheter having a first end dimensioned to be insertable through the cervix and into the uterus and stabilizing means attached adjacent the first end for stabilizing the catheter in the uterus, the catheter having a second end adapted to be attachable to the pump;
    positioning the first end of the catheter in the uterus;
    positioning the stabilizing means in the vagina of the patient;
    selecting the concentration of the sperm containing media and the pumping rate of the pump to deliver between 1 million and 9 million motile sperm per hour; and
    the pump pumping the media into the uterus for at least three hours;
    wherein the stabilizing means comprises an inflatable balloon attached to the catheter adjacent the first end, the balloon being dimensioned to expand sufficiently upon inflation to immobilize the catheter, the balloon being deflatable to allow the removal of the catheter after treatment is completed, and wherein the step of positioning the stabilizing means in the vagina of the patient includes inflating the balloon sufficiently to immobilize the catheter.

9. A method of artificial intrauterine insemination as described in claim 8 wherein the pump is adapted to pump the media in a substantially continuous stream.

10. A method of artificial intrauterine insemination as described in claim 9 wherein the second end of the catheter is releasably attachable to the pump, and wherein the catheter further comprises a balloon inflating tube having a first end connected to the balloon and a second end having a valve for closing off the balloon inflating tube when the balloon is inflated.

11. An artificial intrauterine insemination catheter comprising:
   a) a long flexible tubular body having an internal channel, side walls, a first end dimensioned to pass through a human cervix and into a human uterus and a second end adapted to be releasably coupled to a delivery pump;
   b) an inflatable balloon attached to the body adjacent the first end and dimensioned larger than said first end so as not to pass through the human cervix and also dimensioned to be received in a human vagina;
   c) an inflation tube for inflating the balloon, the inflation tube extending the length of the body and having a first end connected to the balloon and a second end releasably attachable to a balloon inflating pump;
   d) the second end of the inflation tube having a valve for closing and opening the inflation tube;
   wherein the balloon is dimensioned to expand sufficiently upon inflation to immobilize the catheter, and wherein the balloon is deflatable to allow the removal of the catheter after treatment is completed.

12. A catheter as described in claim 11 wherein the second end of the body of the catheter narrows at the first end of the body to form a narrow extension, the narrow extension dimensioned to fit through the cervix and extend into the uterus for at least one cm.

13. A catheter as described in claim 12 wherein the diameter of the body of the catheter is between 4 to 8 mm and wherein the narrow extension of the first end of the catheter has a diameter of between 1.5 to 4 mm and a length of between 4 cm to 7 cm.

14. A catheter as described in claim 13 wherein the body has a separate delivery tube imbedded therein, the delivery tube adapted to deliver a sperm containing media, the delivery tube extending from the second end of the body to the first end of the body.

15. A catheter as described in claim 14 wherein the balloon comprises a hollow in the side wall of the body adjacent the narrow extension, the side wall being made of an elastically deformable material, the diameter of the body of the catheter around the hollow expanding upon inflation of the balloon.

16. A catheter as described in claim 15 wherein the inflation tube is imbedded in the body of the catheter, the second end of the inflation tube exiting the body of the catheter at a point adjacent the second end of the catheter.

17. A device useful in delivery sperm containing media to the uterus of a patient comprising:
   a) a portable pumping means having a reservoir for containing a quantity of the media;
   b) a flexible catheter means for delivering the media from the reservoir to the uterus, the catheter means having a first end dimensioned for insertion into the uterus through the cervix and a second end configured for releasable connection to the pumping means;
   c) the pumping means having an attachment means for releasably attaching the pumping means to the patient;
   d) the pumping means for slowly pumping a volume of the media through the catheter means over several hours, and the pumping means pumping the volume of the media in a series of aliquots; and
   e) releasable retention means attached to the catheter means for releasably retaining the catheter means in the uterus of the patient.

18. The device as defined in claim 17 wherein the releasable retention means comprises a balloon attached to the catheter means adjacent the first end, and further comprising an inflation tube for inflating the balloon, the inflation tube having a first end attached to the balloon and a second end releasably attachable to a balloon inflating pump, the inflation tube having a valve for closing off the inflation tube after inflation of the balloon.

19. The device as defined in claim 18, wherein the balloon is dimensioned to expand sufficiently upon inflation to immobilize the catheter, and wherein the balloon is deflatable to allow the removal of the catheter after treatment is completed.

20. The device as defined in claim 17 wherein the pumping means comprises a syringe and automated syringe driver, the syringe driver adapted to pump the aliquots of the media, and the aliquots pumped by the syringe driver having volumes of between $1 \times 10^{-3}$ ml to $10 \times 10^{-3}$ ml each, the syringe driver being further adapted to pump each aliquot at intervals of between 10 seconds to 1 minute.

21. The device as defined in claim 20 wherein the first end of the catheter is made of silicone rubber and wherein the first end of the catheter is a narrow extension of the catheter, the narrow extension having a diameter of between 1.5 mm to 4 mm and having a length of between 4 cm to 7 cm.

* * * * *